United States Patent
Traneus

(10) Patent No.: US 10,610,700 B2
(45) Date of Patent: Apr. 7, 2020

(54) SYSTEM AND METHOD FOR ION BASED RADIOTHERAPY TREATMENT PLAN EVALUATION

(71) Applicant: RaySearch Laboratories AB, Stockholm (SE)

(72) Inventor: Erik Traneus, Uppsala (SE)

(73) Assignee: RaySearch Laboratories AB, Stockholm (SE)

( * ) Notice: Subject to any disclaimer, the term of this patent is extended or adjusted under 35 U.S.C. 154(b) by 0 days.

(21) Appl. No.: 16/461,116

(22) PCT Filed: Nov. 14, 2017

(86) PCT No.: PCT/EP2017/079107
§ 371 (c)(1),
(2) Date: May 15, 2019

(87) PCT Pub. No.: WO2018/091427
PCT Pub. Date: May 24, 2018

(65) Prior Publication Data
US 2019/0336790 A1    Nov. 7, 2019

(30) Foreign Application Priority Data
Nov. 17, 2016   (EP) ..................... 16199274

(51) Int. Cl.
*A61N 5/10* (2006.01)
*G16H 20/40* (2018.01)
*G16C 20/30* (2019.01)

(52) U.S. Cl.
CPC ............ *A61N 5/103* (2013.01); *G16C 20/30* (2019.02); *G16H 20/40* (2018.01); *A61N 2005/1087* (2013.01)

(58) Field of Classification Search
CPC .... A61N 5/103–1048; A61N 2005/1032–1098
See application file for complete search history.

(56) References Cited

U.S. PATENT DOCUMENTS

| | | | |
|---|---|---|---|
| 2006/0033044 A1 | 2/2006 | Gentry et al. | |
| 2016/0048984 A1 | 2/2016 | Frigo | |
| 2016/0059039 A1* | 3/2016 | Liu ....................... | A61N 5/1039 600/1 |

FOREIGN PATENT DOCUMENTS

| | | | |
|---|---|---|---|
| EP | 3 081 262 A1 | 10/2016 | |
| WO | WO-2004/093971 A2 | 11/2004 | |

(Continued)

OTHER PUBLICATIONS

Böhlen, T.T. et al., "Investigating the robustness of ion beam therapy treatment plans to uncertainties in biological treatment parameters," Physics in Medicine and Biology, 57 (2012) pp. 7983-8004.

(Continued)

*Primary Examiner* — Catherine B Kuhlman
(74) *Attorney, Agent, or Firm* — Faegre Drinker Biddle & Reath LLP

(57) ABSTRACT

A method of evaluating the robustness of a radiotherapy treatment plan for ion based radiotherapy, comprises the steps of: obtaining information related to the incident energy of ions that will stop in each voxel of the treatment volume; calculating a quantity value representative of the incident energy of these ions; and using the quantity values calculated for the first and second portion as a measure of the quality of the radiotherapy treatment plan, in particular its robustness. The information may include the mean incident energy for all ions, and/or an indication of the distribution of the energy values for all the ions.

12 Claims, 2 Drawing Sheets

(56) References Cited

FOREIGN PATENT DOCUMENTS

WO     WO-2005/057738 A2     6/2005
WO     WO-2007/126782 A2     11/2007

OTHER PUBLICATIONS

Chen, Wei et al., "Including Robustness in Multi-criteria Optimization for Intensity Modulated Proton Therapy," Physics in Medicine and Biology, 57(3), 2012, pp. 591-608.
Jan, S. et al., "GATE V6: a major enhancement of the GATE simulation platform enabling modelling of CT and radiotherapy," Physics in Medicine and Biology, 56 (2011) pp. 881-901.
Liu, Wei et al., "Robust optimization of intensity modulated proton therapy," Medical Physics, 39(2), Feb. 2012, pp. 1079-1091.
Malyapa, Robert et al., "Evaluation of Robustness to Setup and Range Uncertainties for Head and Neck Patients Treated With Pencil Beam Scanning Proton Therapy," International Journal of Radiation Oncology Biology Physics, vol. 95, No. 1, 2016, pp. 154-162.
European Search Report / Opinion dated May 4, 2017 for EP 16199274.8.

\* cited by examiner

SYSTEM AND METHOD FOR ION BASED RADIOTHERAPY TREATMENT PLAN EVALUATION

This application is the National Stage of International Application No. PCT/EP2017/079107, filed Nov. 14, 2017, and claims benefit of European Patent Application No. 16199274.8, filed Nov. 17, 2016, the entire contents of which are incorporated by reference herein.

TECHNICAL FIELD

The present invention relates to a method and a system for evaluating an ion based radiotherapy treatment plan, and a computer program product for controlling such a system.

BACKGROUND

In ion based radiotherapy each ion will emit most of its energy towards the end of its path, creating what is known as the Bragg peak. A key issue in treatment planning is to ensure that the Bragg peaks of all beams is placed within the treatment volume, in such a way that all parts of the treatment volume receive the prescribed dose while minimizing dose to the surrounding volume.

The position of the Bragg peak is affected by the kinetic energy Tp of each ion. The values for Tp are selected so that the ions having the lowest energy will stop in an area at the nearest end of the treatment volume and the ions having the highest energy will stop in the area at the farthest end of the treatment volume.

In ion based radiotherapy the ions follow individual paths through the treatment volume from the point of incidence to the point where the ion has lost all its energy and stops. This point is referred to as the "track end". In ion radiotherapy the distribution of track ends is of great interest as the track ends determine the end of range of the treatment field.

Current methods for delivering ion radiotherapy include:
The active scanning technique where the patient irradiation is delivered as a sequence of quasi-monoenergetic "spots" whose energy, direction and weight are selected so that the treatment volume is covered. The active technique is sometimes referred to as pencil beam scanning (PBS).
The passive technique, i.e. where the patient is irradiated by broad fields where the direction, incident energy and lateral extension is modulated so that the treatment volume is covered. The passive technique can be realized by several technical solutions. Examples are double scattering (DS), uniform scanning (US) or wobbling.

The present invention is applicable to all current methods for delivering ion radiotherapy.

Throughout this document both the active scanning technique and the passive technique will be discussed. For the sake of simplicity, these will sometimes be referred to as just PBS and DS, respectively, as the most prominent examples of the respective technique.

For a PBS plan the spots in a beam can be grouped in "energy layers" during the process of creating the plan. All spots in an energy layer have the same incident energy spectrum. An energy layer can be assigned an index (the control point index) and a nominal energy (the control point energy).

For a DS plan the energy of the ions is delivered as single irradiation field per beam. In this field the ion energies are distributed over an energy range defined so that the Bragg peaks fall between the shallowest part and the most distal part of the treatment volume. The incident energy is further laterally range modulated by a compensator and collimated by an aperture.

For a DS plan there are usually no energy layers in the same way as there are for a PBS plan, but it is still possible for a passive technique plan to group the incident energies into energy layers.

It should be understood throughout this document that when describing the invention and when there is no distinction essential for the purpose of the invention needed between the active and passive techniques we will use the term energy layer in this broader sense.

There are uncertainty factors due to CT calibration, tissue inhomogeneity, organ motion and deformation. Because of such uncertainty factors there is a desire for a plan to be as robust as possible, meaning that it should provide the same dose distribution even if some factor changes. It is important to evaluate the quality of a radiotherapy treatment plan, to ensure that it will be delivered correctly and affect the patient in the desired way. When evaluating a radiotherapy treatment plan, its robustness is a key factor. The robustness reflects how well the plan will work in the case of small changes to the setup. For example, if the patient receiving the treatment moves relative to the assumed position this will affect where the particles will stop and thereby also the treatment.

Current methods for determining robustness include
displaying beam dose per energy layer. In this case the dose distribution for a single energy layer is shown for each image
displaying Bragg peak positions for the ions.

SUMMARY OF THE INVENTION

It is an object of the present invention to improve and facilitate analysis of the quality of an ion treatment plan with respect to for example robustness.

The invention relates to a method of evaluating a radiotherapy treatment plan for ion based radiotherapy, comprising the steps, for each of at least a first and a second portion in a treatment volume, of
Obtaining information related to the incident energy of ions that will stop in the portion,
Calculating a quantity value representative of the incident energy of the ions that will stop in the portion,
Using the quantity values calculated for the first and second portion as a measure of the quality of the radiotherapy treatment plan, in particular its robustness.

Typically, the portions of the treatment volume are dose calculation voxels, but the portions may also be defined in another way, for example, as a group of dose calculation voxels. It should be understood throughout this document that instead of voxels in the strict sense, the method could be applied to other types of portions of the treatment volume. Normally, however, dose calculation voxels are used as a suitable division of the treatment volume for practical purposes.

Preferably the steps are performed for a plurality of portions and the step of using the calculated quantity values comprises determining a distribution of the quantity values.

The quantity values characterize the penetration range of the ions belonging to one energy layer. This quantity value may be an average control point index at track ends or average nominal energy at track ends. The quantities calculated may be used by the system to determine if the robustness of the plan is satisfactory and the system can then simply indicate the result of the evaluation. Preferably, however, the data are visualized and displayed to a user, who may use the displayed data to determine if any changes are needed to the plan, and in that case, how the changes should be implemented. Different ways of visualizing the data are discussed below.

The invention enables a clear visualization of the distribution of the range per energy layer within the patient anatomy, which may be used to evaluate the robustness of the treatment plan. Further, the visualization also enables a clear visualization of the depth range reached per energy layer through the width of the characteristic bands. According to the invention, a single representation will show the entire result of the energy layer distribution of the plan in a manner that is consistent with how the ions are propagating though the medium. This is an improvement over methods based on beam doses, or on Bragg peak positions. In the former case the result is obtained as a series of visualizations and not in a composite image. In the latter case only the geometrical trace along the central ray of the spot is shown.

In one embodiment, particularly suited for active techniques such as PBS, the step of using the quantity as a quality measure includes:
  Assigning each of the calculated quantity values to one of a number of energy layers, and
  Displaying for each of the at least first and second portion of the treatment volume, information representing the energy layers to which the calculated quantity values are assigned.

In an alternative embodiment, particularly suited for passive techniques, the step of using the quantity as a quality measure includes:
  Assigning each of the calculated quantity values to one of a number of discrete or continuous labelled virtual energy layers, and
  Displaying for each of the at least first and second portion of the treatment volume, information representing the energy layers to which the calculated quantity values are assigned.

Preferably, the information related to the quantity values for ions that will stop in the portion of the treatment volume includes a value indicating the combined quantity values of all ions that will stop in the portion of the treatment volume, as this will provide the most accurate accumulated values. Alternatively, only information related to some of the ions will be used, which will save computational resources.

The quantity representative of the incident energy of the ions may also include an average of the quantity values of the ions that will stop in the portion of the treatment volume, such as average control point index or average nominal energy of the ion in the portion of the treatment volume where it stops.

The quantity representative of the incident energy of the ions may include a measure of the spread of the quantity values of the ions that will stop in the portion of the treatment volume, such as one standard deviation of the control point index or one standard deviation nominal energy of the ion in the portion of the treatment volume where it stops The quantity representative of the energy of the ions may also, or alternatively, include a value representing a distribution measure of the quantity values of individual ions that will stop in the portion of the treatment volume. Such a value will be indicative of the spread in incident energies of particles that stop in the same voxel, which in turn is indicative of the robustness of the plan.

In one embodiment, the method uses a radiation transport method to accumulate energy layer specific data for each dose voxel where protons stop. This data can be, for example,
  Energy layer control point index at track ends
  Nominal control point energy at track ends
  Sampled source ion energy per energy layer at track ends, e.g. in units of Mev/u.

The energy layer control point index is a set of integers, each representing one of the energy layers, in range 1 to the number of energy layers.

The nominal control point energy is a set of real numbers, each representing one of the energy layers e.g. in units of MeV/u.

The sample source ion energy per energy layer is relevant when a Monte Carlo dose engine is used.

An alternative method would be to calculate a dose distribution for each energy layer, using a suitable radiation transport method, as discussed below, and to display a line joining the maximum dose per energy layer. This would provide similar but less condensed information indicative of the robustness of the plan.

Radiation transport methods as such are known in the art and are included in radiotherapy systems for other purposes such as calculating dose distributions. Radiation transport methods for calculating a dose distribution is referred to as "dose calculation engine" and may use, for example, the Monte Carlo algorithm or the pencil beam algorithm. Using a dose calculation engine to calculate the quantity ensures that all relevant effects (density inhomogeneity, lateral scattering and energy straggling) are accurately accounted for, using the same physics as for dose computation. Also, the data can be provided with practically no additional computational charge during a regular dose calculation. Alternatively, the quantity may be computed using a dedicated calculation algorithm that is capable of modelling radiation transport in patient anatomies with sufficient accuracy.

The resulting accumulated quantity values may be displayed in any suitable way. In a preferred embodiment, each energy layer is assigned a colour and the step of displaying information representing the energy layer includes displaying a representation of the treatment volume, where each of the at least first and second portions of the treatment volume is displayed in the colour representing the energy layer to which the portion of the treatment volume is assigned.

An alternative method of displaying the result will be a 3D representation, wherein each energy band is assigned an elevation level and the step of displaying information representing the energy band includes displaying a 3-dimensional representation of the treatment volume, where each of the at least first and second portions of the treatment volume is displayed at the elevation level representing the energy band to which the portion of the treatment volume is assigned. It will also be possible to simply superimpose borders between energy layers, preferably with numbers indicating the accumulated quantity value for each energy layer.

It should be understood throughout this document that instead of voxels in the strict sense, the method could be applied to other types of portions of the treatment volume. Normally, however, dose calculation voxels are used as a suitable division of the treatment volume for practical purposes.

The invention also relates to a computer program product comprising computer readable code means which, when executed in a computer, will cause the computer to perform the method according to any one of the preceding claims.

The invention also relates to a non-transitory computer readable medium encoded with computer executable instructions which, when run in a first computer device will cause the device to perform the method according to any one of the preceding claims.

The invention also relates to a computer system comprising a processor, a data memory and a program memory, wherein the program memory comprises a computer program product according or a non-transitory computer readable medium according to the above.

BRIEF DESCRIPTION OF THE DRAWINGS

The invention will be described in more detail in the following, by way of example and with reference to the appended drawings, in which.

DETAILED DESCRIPTION OF EMBODIMENTS

Figure 1:
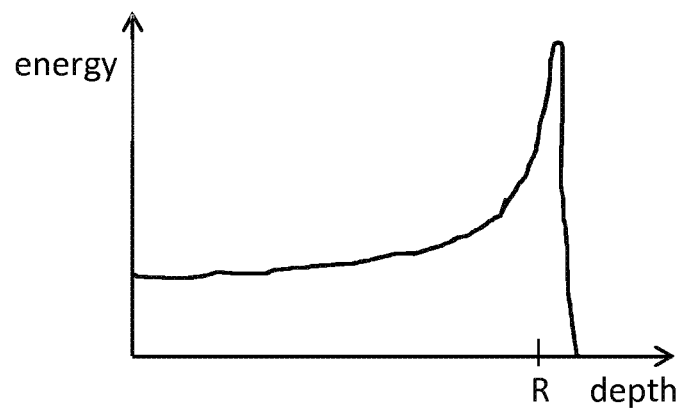
FIG. 1 is an illustration of the Bragg peak.

FIG. 1 illustrates an example Bragg curve which represents the energy deposition of an ion propagating trough a medium, as a function of the distance travelled from the point of incidence to its maximum range R. The actual shape and amplitude will vary for different types of ions and media, but the general shape will be as shown in FIG. 1. As can be seen, the main part of the ion's energy will be deposited towards the end of the ion's path in the peak which is commonly referred to as the Bragg peak.

Hence, the Bragg curve helps to predict where the energy of the ions will be deposited. Radiotherapy should be planned such that the Bragg peaks of the different beams are placed such that all parts of the treatment volume will receive the prescribed dose while minimizing dose to regions outside of the treatment volume.

The dose D delivered to a volume will be:

$$D = E/m$$

where E is the energy deposited in the volume and m is the mass of the material in the volume. The deposited energy depends on the kinetic energy of the ion, the type of ion and the composition of the material. The ions used will have incident energies ranging from Tmin to Tmax, where Tmin is the energy needed to place the Bragg peak at the nearest end of the treatment volume and Tmax is the energy needed to place the Bragg peak at the farthest end of the treatment volume.

Because of inhomogeneities such as bone, air cavities, or other structural variations in a patient's body, ions will be scattered and/or slowed down differently in the volume depending on the ion's incident point and direction. The distribution of track ends will vary depending on the type of structural variation. Therefore, determining the energy deposited by the ions and the track end positions is generally not straightforward.

Figure 2A:
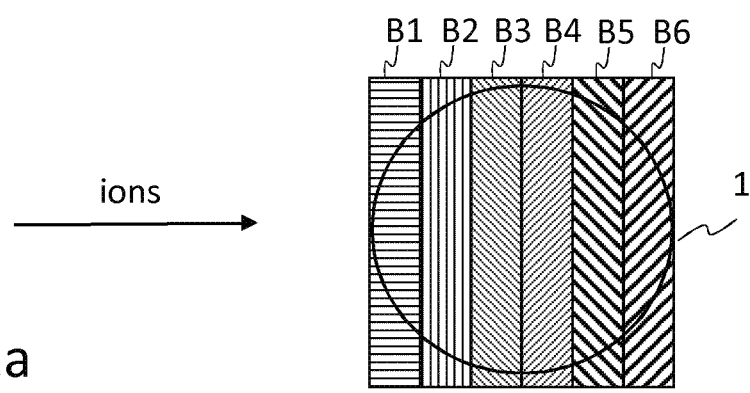
FIGS. 2a and 2b illustrate the distribution of energy layers in a treatment volume in an ideal situation and a more realistic situation, respectively.

FIG. 2a shows the distribution of the quantity (in this example computed as the average control point index at track ends for a proton PBS plan) in a treatment volume 1, in an ideal situation, where the ions pass through a completely homogenous medium with a flat external surface. The direction of the incoming ions is perpendicular to the surface of the medium as indicated by the horizontal arrow. The six different energy layers B1-B6 are identified by different patterns: horizontal lines, vertical lines, and four different patterns of diagonal lines. As can be seen, each energy layer forms a band of track ends throughout the treatment volume substantially parallel to the surface of incidence of the ions. This illustrates that all ions belonging to the same energy layer will travel through the treatment volume substantially along paths of similar length, a distance which correlates to their incident kinetical energy Tp.

Figure 2B:
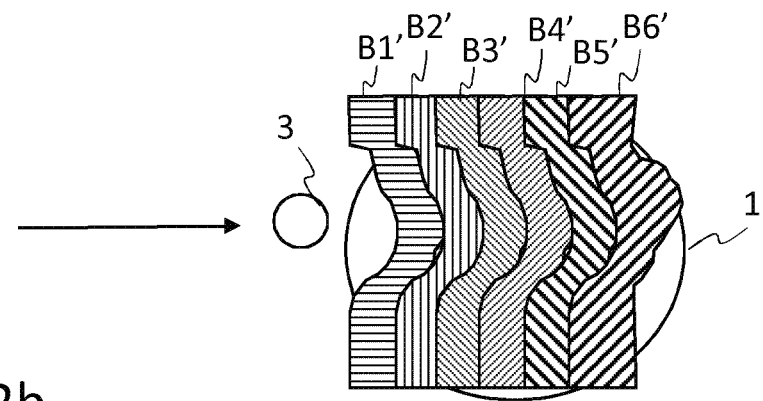

FIG. 2b shows the distribution of the quantity in a patient volume. There is a low density region 3, such as an air cavity, which is in the path of the ions. This will cause ions with the same energy to travel along different paths, causing them to follow different directions and/or path lengths, causing the track end distribution of ions belonging to a specific energy layer to take on a more irregular shape, as illustrated by the energy layers B1'-B6'. As can be seen, there is a ripple, caused by the ions propagating through the low density volume.

Images such as the ones in FIGS. 2a and 2b provide an indication of the regularity of the energy layer versus track end position correlation and, as a consequence, of the disturbance of the ions propagating through the volume. A high amount of ripple or irregular shape of the energy layer vs. track end bands indicates a lower robustness of the plan, in that a small movement of the patient, or other change to the setup, may cause a significant variation in the dose distribution and distribution of track ends actually delivered to the patient.

Figure 3:
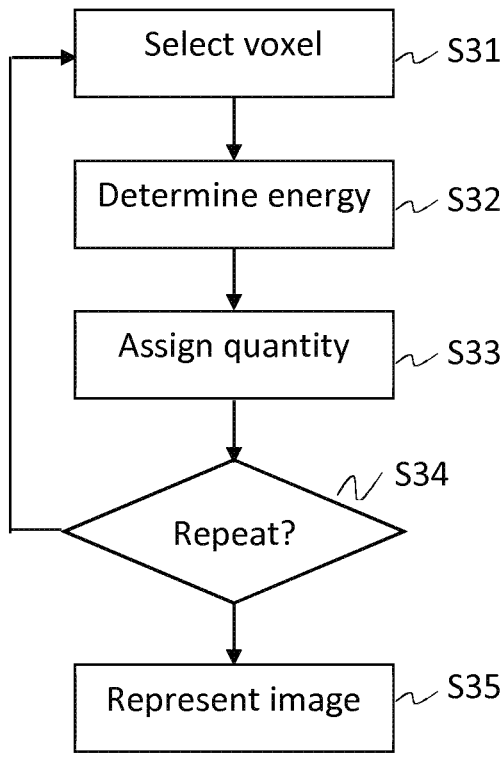
FIG. 3 is a flow chart of a method according to an embodiment of the invention.

FIG. 3 is a flow chart illustrating the principle of a method according to the invention using a Monte Carlo based dose engine. The method is carried out separately for each portion of the treatment volume, typically for each voxel of the treatment volume.

In step S31, a voxel in the treatment volume is selected. In step S32, a value of a quantity representative of the incident energy of the ion is determined. This value can be for example the index of the energy layer to which this proton belongs. In step S33 this voxel is assigned an accumulated quantity value characterizing the accumulated quantity values for all ions that stop in this voxel. It is also possible to base the accumulated quantity value on a certain selection of the ions that stop in the voxel. In step S34 it is determined if the procedure should be repeated for another voxel. Typically, steps S31-S33 are performed for a large number of voxels. In step S35 the accumulated quantity values for all voxels are represented, typically as superimposed information in an image representing the treatment volume. This may be achieved by any suitable visualization method. A simple method would be to present a number representing the quantity for each region, or a selection of regions, of the image. One particularly suitable method includes superpositioning colours onto the voxels of the treatment volume in the image, each colour being selected to identify a particular energy layer. The image may be similar to that shown in FIG. 2a or 2b, but normally with colour coding instead of the patterns shown in the Figures.

An alternative visualization method includes displaying the image as a 3d-image. In this case, instead of a colour, an elevation level is assigned to each energy level, and the elevation level corresponding to each region will be displayed superimposed on the image.

The shape of the layers representing the quantity distribution may be used to determine the robustness of the treatment plan. If the energy layers have a regular shape, the plan is considered to be robust. The more irregularity or ripple displayed by the energy layers, the less robust the plan will be. The shapes of the energy layers will also indicate which parts of the plan will be the least robust, for example if there is a particular area of the treatment volume that will be more affected by irregularities than other areas. This information may be used to change the plan, for example to use another radiation field or to increase the margins.

The shape of the layers representing the quantity distribution may be used to derive a robustness index based on the values of the quantity in a region (e.g. a sphere with a certain radius) surrounding the point of interest (e.g. a dose voxel). This robustness index can be reported by numbers or through images.

The quantity characterizing the incident energy can be, for example, average energy layer index or average nominal energy of each ion at the end of its track. In the case of a Monte Carlo dose engine it could also be the actual sampled energy per sampled ion.

Instead of, or in addition to the accumulated quantity value calculated in step S33, a distribution value indicating the distribution or spread of individual the quantity values determined in step S32. For example, the difference between the highest and the lowest incident energy may be taken into account. If this difference is small, this indicates a robust plan. A larger difference indicates that the ions take many different paths within the volume, which indicates that the plan is less robust.

Figure 4:
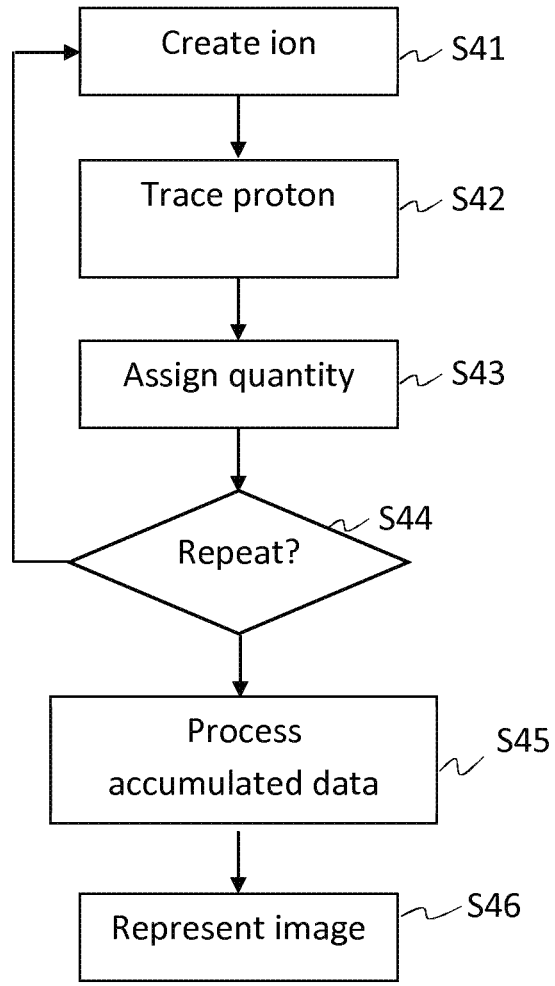
FIG. 4 is a flow chart of a method according to another embodiment of the invention.

FIG. 4 is a flow chart of an alternative embodiment of the method of FIG. 3, as it might be carried out in an existing dose engine. This embodiment is particularly suited for a Monte Carlo dose calculation engine. In step S41 an ion is created. In step S42 the ion is followed along its path until it stops, and its track end position is determined. In step S43 data related to the incident energy of the ion are gathered, for example, the control point index $CP_i$ for each ion is determined. In step S44, it is determined if steps S41-S43 should be repeated for another ion. If yes, the process returns to step S41; if no, the process continues with step S45. In step S45, data accumulated for all ions that stop in each particular voxel, or for a selection of such ions are processed. The result will be an accumulated quantity value for each of the voxels, each accumulated quantity value representing the incident energy of the ions that stop in a particular voxel. Typically, as for FIG. 3, the accumulated quantity will be a mean value of the incident energy for all ions considered, but it can also be representative of the variations of incident energy for ions that stop within a voxel. In step S46, the accumulated data are represented in a suitable way, as discussed for step S35.

As an example, if the data collected in Step S32 is the control point index, the quantity used will be the mean value of the control point index. As will be understood, the standard deviation of this mean value may be considered as a further indicator of robustness.

Determining the combined incident energy of the ions that will stop in a voxel, or the energy of each such ion, may be carried out by means of a dose calculation engine. Such dose calculation engines are commonly present in radiotherapy systems. Dose calculation is based on a patient module typically created by mapping CT intensity values to mass densities in a manner known in the art. When mass densities have been established, material properties are assigned according to what is likely to occur in a human body. From the material properties, quantities relevant to the dose calculation are derived such as stopping power and scattering power. It is also possible to assign material overrides which take precedence over the materials derived from the image data.

As the skilled person will realize, the actual order in which data items are collected and processed is not essential to the invention, and will vary with the delivery method and the dose calculation engine used in each case. Typically, when a Monte Carlo dose calculation engine is used, the calculations for all voxels will be performed in parallel and will be presented simultaneously, as in FIG. 4.

As the skilled person will realize, the data may also be obtained by using a dose engine based on analytical or semi-analytical or numerical transport equation solver.

Figure 5:
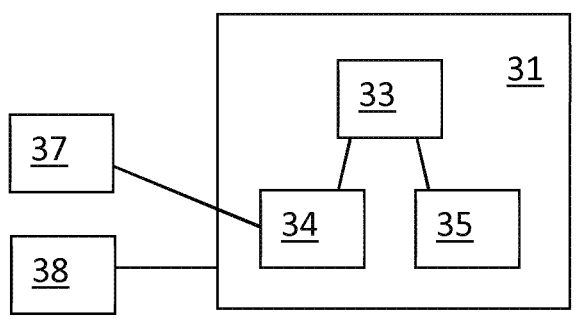
FIG. 5 illustrates a computer system in which the inventive method may be implemented.

FIG. 5 is a schematic representation of a computer system in which the inventive method may be performed. A computer 31 comprises a processor 33, a data memory 34 and a program memory 35. Preferably, a user input means 37, 38 is also present, in the form of a keyboard, a mouse, a joystick, voice recognition means or any other available user input means. The user input means may also be arranged to receive data from an external memory unit.

A treatment plan to be evaluated is found in the data memory 34. The treatment plan may be generated in the computer 31, or received from another storage means in any way known in the art.

The data memory 34 also holds deposited ion energy information for each voxel. As will be understood, the data memory 34 is only shown schematically. There may be several data memory units, each holding one or more different types of data, for example, one data memory for the treatment plan, one for the CT scans, etc.

The program memory 35 holds a computer program arranged to control the processor to perform the plan evaluation according to the invention.

The invention claimed is:

1. A method of displaying results of an evaluation of a radiotherapy treatment plan for ion based radiotherapy on a computer system, the method comprising the steps, for at least a portion in a treatment volume, of:
    obtaining from data memory information related to incident energy of ions that will stop in the portion;
    calculating quantity values representative of the incident energy of the ions that will stop in the portion;
    storing the calculated quantity values in the data memory; and
    using the quantity values calculated for the portion as a measure of the robustness of the radiotherapy treatment plan the using step comprising:
        assigning each of the calculated quantity values in the data memory to one of a number of energy layers; and
        displaying for the portion of the treatment volume, a representation of the treatment volume and a visualization representing the energy layers in the representation of the treatment volume to which the calculated quantity values are assigned.

2. The method according to claim 1, wherein the steps are performed for a plurality of portions in the treatment volume and the step of using the calculated quantity values comprises determining a distribution of the quantity values.

3. The method according to claim 1, wherein the step of assigning each of the calculated quantity values includes assigning each of the calculated quantity values to one of a number of discrete or continuous labelled virtual energy layers.

4. The method according to claim 1, wherein the information related to incident energy comprises at least one of the following:
   energy layer control point index;
   nominal control point energy; or
   actual sampled energy per sampled ion.

5. The method according to claim 1, wherein the information related to the incident energy of ions that will stop in the portion of the treatment volume includes a value indicating the combined quantity values of all ions that will stop in the portion of the treatment volume.

6. The method according to claim 1, wherein the quantity value representative of the incident energy of the ions includes an average of the quantity values of the ions that will stop in the portion of the treatment volume.

7. The method according to claim 6, wherein the average of the quantity values is either an average control point index or an average nominal energy of the ion in the portion of the treatment volume where it stops.

8. The method according to claim 1, wherein the quantity values representative of the incident energy of the ions includes a value representing the difference between the quantity values of individual ions that will stop in the portion of the treatment volume.

9. The method according to claim 1, wherein each energy layer is assigned a colour and the step of displaying includes displaying the portion of the treatment volume in the colour representing the energy layer to which the portion of the treatment volume is assigned.

10. The method according to claim 1, wherein each energy layer is assigned an elevation level and the representation of the treatment volume in the step of displaying is a 3-dimensional representation of the treatment volume, where the portion of the treatment volume is displayed at the elevation level representing the energy layer to which the portion of the treatment volume is assigned.

11. A non-transitory computer readable medium encoded with computer executable instructions which, when run in a first computer device will cause the device to perform the method according to claim 1.

12. A computer system comprising a processor, a data memory, and a program memory, wherein the program memory comprises the non-transitory computer readable medium encoded with computer executable instructions according to claim 11.

\* \* \* \* \*